US012776406B2

(12) United States Patent
Vik et al.

(10) Patent No.: US 12,776,406 B2
(45) **Date of Patent: *Oct. 27, 2026**

(54) DISPLAYING VISUAL ELEMENTS ON A MEDICAL DEVICE

(71) Applicant: CareFusion 303, Inc., San Diego, CA (US)

(72) Inventors: Daniel Vik, Sunnyvale, CA (US); Sreelal Chandrasenan, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/399,191

(22) Filed: Nov. 24, 2025

(65) Prior Publication Data

US 2026/0080998 A1 Mar. 19, 2026

Related U.S. Application Data

(63) Continuation of application No. 18/978,664, filed on Dec. 12, 2024, now Pat. No. 12,482,549, which is a (Continued)

(51) Int. Cl.
*G09G 5/00* (2006.01)
*A61M 5/142* (2006.01)
(Continued)

(52) U.S. Cl.
CPC ............ *G16H 20/17* (2018.01); *A61M 5/142* (2013.01); *G06F 3/04847* (2013.01); *G09G 5/00* (2013.01);
(Continued)

(58) Field of Classification Search
CPC ....... G16H 20/17; G16H 40/63; A61M 5/142; A61M 2205/505; G06F 3/04847; G09G 5/00; G09G 2380/08; G06T 2210/41
See application file for complete search history.

(56) References Cited

U.S. PATENT DOCUMENTS

| | | |
|---|---|---|
| 5,331,549 A | 7/1994 | Crawford, Jr. |
| 5,531,697 A | 7/1996 | Olsen et al. |

(Continued)

FOREIGN PATENT DOCUMENTS

| | | |
|---|---|---|
| CA | 2967856 A1 | 10/2009 |
| CN | 1784684 A | 6/2006 |

(Continued)

OTHER PUBLICATIONS

AIV. (Apr. 16, 2012). "Hospira IV Pumps Obtain Highest KLAS scores." Medwrench. 1 page.

(Continued)

*Primary Examiner* — Antonio A Caschera
(74) *Attorney, Agent, or Firm* — Mintz Levin Cohn Ferris Glovsky and Popeo, P.C.

(57) ABSTRACT

A medical system includes a medical device and a display for displaying a plurality of visual elements. The plurality of visual elements are associated with functions of the medical device. The medical system also includes a plurality of visual profiles for facilitating in controlling visual appearance of the plurality of visual elements displayed on the display, and a visual profile selector for selecting at least one of the plurality of visual profiles based on a state of the medical device.

30 Claims, 3 Drawing Sheets

Related U.S. Application Data continuation of application No. 18/678,556, filed on May 30, 2024, now Pat. No. 12,205,703, which is a continuation of application No. 17/539,526, filed on Dec. 1, 2021, now Pat. No. 12,205,700, which is a continuation of application No. 15/930,270, filed on May 12, 2020, now Pat. No. 11,217,338, which is a continuation of application No. 16/197,121, filed on Nov. 20, 2018, now Pat. No. 10,664,147, which is a continuation of application No. 14/939,875, filed on Nov. 12, 2015, now Pat. No. 10,140,004, which is a continuation of application No. 12/987,472, filed on Jan. 10, 2011, now Pat. No. 9,190,010.

(51) Int. Cl.
*G06F 3/04847* (2022.01)
*G16H 20/17* (2018.01)
*G16H 40/63* (2018.01)

(52) U.S. Cl.
CPC ....... *G16H 40/63* (2018.01); *A61M 2205/505* (2013.01); *G09G 2320/066* (2013.01); *G09G 2320/0666* (2013.01); *G09G 2340/14* (2013.01); *G09G 2360/144* (2013.01); *G09G 2380/08* (2013.01)

(56) References Cited

U.S. PATENT DOCUMENTS

| | | | |
|---|---|---|---|
| 5,637,093 | A | 6/1997 | Hyman et al. |
| 5,764,034 | A | 6/1998 | Bowman et al. |
| 5,782,805 | A | 7/1998 | Meinzer et al. |
| 5,883,576 | A | 3/1999 | De La Huerga |
| 5,952,992 | A | 9/1999 | Helms |
| 6,082,620 | A | 7/2000 | Bone, Jr. |
| 6,094,185 | A | 7/2000 | Shirriff |
| 6,406,426 | B1 | 6/2002 | Reuss et al. |
| 6,475,180 | B2 | 11/2002 | Peterson et al. |
| 6,519,569 | B1 | 2/2003 | White et al. |
| 6,529,212 | B2 | 3/2003 | Miller et al. |
| 6,671,563 | B1 | 12/2003 | Engelson et al. |
| 6,751,657 | B1 | 6/2004 | Zothner |
| 6,877,661 | B2 | 4/2005 | Webb et al. |
| 6,985,870 | B2 | 1/2006 | Martucci et al. |
| 7,155,729 | B1 | 12/2006 | Andrew et al. |
| 7,301,451 | B2 | 11/2007 | Hastings |
| 7,387,250 | B2 | 6/2008 | Muni |
| 7,417,729 | B2 | 8/2008 | Greenwald |
| 7,434,724 | B2 | 10/2008 | Lane |
| 7,933,780 | B2 | 4/2011 | De La Huerga |
| 7,942,844 | B2 | 5/2011 | Moberg et al. |
| 7,976,508 | B2 | 7/2011 | Hoag |
| 7,978,564 | B2 | 7/2011 | De La Huerga |
| 8,065,161 | B2 | 11/2011 | Howard et al. |
| 8,172,798 | B2 | 5/2012 | Hungerford et al. |
| 8,235,938 | B2 | 8/2012 | Eggers et al. |
| 8,287,495 | B2 | 10/2012 | Michaud et al. |
| 8,352,290 | B2 | 1/2013 | Bartz et al. |
| 8,359,338 | B2 | 1/2013 | Butterfield et al. |
| 8,486,019 | B2 | 7/2013 | White et al. |
| 8,504,179 | B2 | 8/2013 | Blomquist |
| 8,514,086 | B2 | 8/2013 | Harper et al. |
| 8,551,038 | B2 | 10/2013 | Tsoukalis |
| 8,567,681 | B2 | 10/2013 | Borges et al. |
| 8,775,196 | B2 | 7/2014 | Simpson et al. |
| 8,894,631 | B2 | 11/2014 | McTaggart et al. |
| 8,912,990 | B2 | 12/2014 | Vieri et al. |
| 8,961,461 | B2 | 2/2015 | Stewart et al. |
| 8,990,722 | B2 | 3/2015 | Gannon et al. |
| 8,998,100 | B2 | 4/2015 | Halbert et al. |
| 9,053,520 | B2 | 6/2015 | Vik et al. |
| 9,098,604 | B2 | 8/2015 | Treacy |
| 9,183,603 | B2 | 11/2015 | Borges et al. |
| 9,190,010 | B2 | 11/2015 | Vik et al. |
| 9,192,721 | B2 | 11/2015 | Vavala et al. |
| 9,213,928 | B2 | 12/2015 | Neff |
| 9,356,888 | B2 | 5/2016 | Gross et al. |
| 9,390,235 | B2 | 7/2016 | Naker et al. |
| 9,530,087 | B2 | 12/2016 | Borges et al. |
| 9,547,751 | B2 | 1/2017 | Vik et al. |
| 9,971,871 | B2 | 5/2018 | Arrizza et al. |
| 10,089,442 | B2 | 10/2018 | Van Zon et al. |
| 10,130,815 | B2 | 11/2018 | Singal et al. |
| 10,140,004 | B2 | 11/2018 | Vik et al. |
| 10,275,571 | B2 | 4/2019 | Coffman et al. |
| 10,380,321 | B2 | 8/2019 | Kamen et al. |
| 10,453,157 | B2 | 10/2019 | Kamen et al. |
| 10,503,871 | B2 | 12/2019 | Naker et al. |
| 10,635,784 | B2 | 4/2020 | Rubalcaba et al. |
| 10,664,147 | B2 | 5/2020 | Vik et al. |
| 11,210,611 | B2 | 12/2021 | Kamen et al. |
| 11,217,338 | B2 | 1/2022 | Vik et al. |
| 11,244,745 | B2 | 2/2022 | Kamen et al. |
| 11,289,180 | B2 | 3/2022 | Vik et al. |
| 11,324,880 | B2 | 5/2022 | Garibaldi et al. |
| 11,555,729 | B2 | 1/2023 | Naker et al. |
| 11,901,058 | B2 | 2/2024 | Vik et al. |
| 11,943,309 | B2 | 3/2024 | Orona et al. |
| 12,028,414 | B1 | 7/2024 | Borges et al. |
| 12,205,700 | B2 | 1/2025 | Vik et al. |
| 12,205,703 | B2 * | 1/2025 | Vik ........................ G16H 20/17 |
| 12,278,868 | B2 | 4/2025 | Borges et al. |
| 2002/0019714 | A1 | 2/2002 | Carliale et al. |
| 2002/0038392 | A1 | 3/2002 | De La Huerga |
| 2002/0071076 | A1 | 6/2002 | Webb et al. |
| 2002/0087113 | A1 | 7/2002 | Hartlaub |
| 2002/0099273 | A1 | 7/2002 | Bocionek et al. |
| 2002/0188259 | A1 | 12/2002 | Hickle et al. |
| 2002/0193679 | A1 | 12/2002 | Malave et al. |
| 2003/0009244 | A1 | 1/2003 | Engleson et al. |
| 2003/0040700 | A1 | 2/2003 | Hickle et al. |
| 2003/0069614 | A1 | 4/2003 | Bowman et al. |
| 2003/0135388 | A1 | 7/2003 | Martucci et al. |
| 2003/0139701 | A1 | 7/2003 | White et al. |
| 2003/0140928 | A1 | 7/2003 | Bui et al. |
| 2003/0140929 | A1 | 7/2003 | Wilkes et al. |
| 2003/0141981 | A1 | 7/2003 | Bui et al. |
| 2003/0144878 | A1 | 7/2003 | Wilkes et al. |
| 2003/0173405 | A1 | 9/2003 | Wilz et al. |
| 2003/0200117 | A1 | 10/2003 | Manetta et al. |
| 2004/0002958 | A1 | 1/2004 | Seshadri et al. |
| 2004/0019464 | A1 | 1/2004 | Martucci et al. |
| 2004/0030323 | A1 | 2/2004 | Ullestad et al. |
| 2004/0032426 | A1 | 2/2004 | Rutledge et al. |
| 2004/0051368 | A1 | 3/2004 | Caputo et al. |
| 2004/0068481 | A1 | 4/2004 | Seshadri et al. |
| 2004/0078231 | A1 | 4/2004 | Wilkes et al. |
| 2004/0121767 | A1 | 6/2004 | Simpson et al. |
| 2004/0167465 | A1 | 8/2004 | Mihai et al. |
| 2004/0167804 | A1 | 8/2004 | Simpson et al. |
| 2004/0172222 | A1 | 9/2004 | Simpson et al. |
| 2004/0172301 | A1 | 9/2004 | Mihai et al. |
| 2004/0172302 | A1 | 9/2004 | Martucci et al. |
| 2004/0176667 | A1 | 9/2004 | Mihai et al. |
| 2004/0193325 | A1 | 9/2004 | Bonderud et al. |
| 2004/0193453 | A1 | 9/2004 | Butterfield et al. |
| 2004/0249674 | A1 | 12/2004 | Eisenberg et al. |
| 2005/0038332 | A1 | 2/2005 | Saidara et al. |
| 2005/0055242 | A1 | 3/2005 | Bello et al. |
| 2005/0055244 | A1 | 3/2005 | Mullan et al. |
| 2005/0065817 | A1 | 3/2005 | Mihai et al. |
| 2005/0095063 | A1 | 5/2005 | Fathallah et al. |
| 2005/0101844 | A1 | 5/2005 | Duckert et al. |
| 2005/0108057 | A1 | 5/2005 | Cohen et al. |
| 2005/0140498 | A1 | 6/2005 | Bastian, II |
| 2005/0144043 | A1 | 6/2005 | Holland et al. |
| 2005/0171512 | A1 | 8/2005 | Flaherty |
| 2005/0177395 | A1 | 8/2005 | Blomquist |
| 2005/0267402 | A1 | 12/2005 | Stewart et al. |
| 2005/0278194 | A1 | 12/2005 | Holland et al. |
| 2006/0026205 | A1 | 2/2006 | Butterfield |
| 2006/0081257 | A1 | 4/2006 | Krogh et al. |

(56) References Cited

U.S. PATENT DOCUMENTS

| | | | |
|---|---|---|---|
| 2006/0098666 | A1 | 5/2006 | Francis Conde Powell |
| 2006/0116639 | A1 | 6/2006 | Russell |
| 2006/0119574 | A1 | 6/2006 | Richardson et al. |
| 2006/0119754 | A1 | 6/2006 | Hirakata et al. |
| 2006/0154642 | A1 | 7/2006 | Scannell |
| 2006/0167722 | A1 | 7/2006 | MRF Struys et al. |
| 2006/0189926 | A1 | 8/2006 | Hall et al. |
| 2006/0206356 | A1 | 9/2006 | Vanderveen |
| 2006/0229551 | A1 | 10/2006 | Martinez et al. |
| 2006/0229557 | A1 | 10/2006 | Fathallah et al. |
| 2007/0041626 | A1 | 2/2007 | Weiss et al. |
| 2007/0098565 | A1 | 5/2007 | Parsee et al. |
| 2007/0100282 | A1 | 5/2007 | Small et al. |
| 2007/0124002 | A1 | 5/2007 | Estes et al. |
| 2007/0124177 | A1 | 5/2007 | Engleson et al. |
| 2007/0145137 | A1 | 6/2007 | Mrowiec |
| 2007/0197974 | A1 | 8/2007 | Gibson |
| 2007/0210157 | A1 | 9/2007 | Miller |
| 2007/0214003 | A1 | 9/2007 | Holland et al. |
| 2007/0233050 | A1 | 10/2007 | Wehba et al. |
| 2007/0233521 | A1 | 10/2007 | Wehba et al. |
| 2007/0251835 | A1 | 11/2007 | Mehta et al. |
| 2007/0254593 | A1 | 11/2007 | Jollota et al. |
| 2007/0258395 | A1 | 11/2007 | Jollota et al. |
| 2007/0267475 | A1 | 11/2007 | Hoglund et al. |
| 2007/0287931 | A1 | 12/2007 | Dilorenzo |
| 2008/0033360 | A1 | 2/2008 | Evans et al. |
| 2008/0071251 | A1 | 3/2008 | Moubayed et al. |
| 2008/0086333 | A1 | 4/2008 | Hertel et al. |
| 2008/0125657 | A1 | 5/2008 | Chomas et al. |
| 2008/0133265 | A1 | 6/2008 | Silkaitis et al. |
| 2008/0148040 | A1 | 6/2008 | Machani et al. |
| 2008/0149701 | A1 | 6/2008 | Lane |
| 2008/0154177 | A1 | 6/2008 | Moubayed et al. |
| 2008/0155454 | A1 | 6/2008 | Balasubramanian |
| 2008/0200868 | A1 | 8/2008 | Alberti et al. |
| 2008/0201169 | A1 | 8/2008 | Galasso et al. |
| 2008/0275422 | A1 | 11/2008 | Ross |
| 2008/0281167 | A1 | 11/2008 | Soderberg et al. |
| 2008/0283609 | A1 | 11/2008 | Nakajima et al. |
| 2008/0294142 | A1 | 11/2008 | Patel et al. |
| 2008/0294294 | A1 | 11/2008 | Blomquist |
| 2008/0300572 | A1 | 12/2008 | Rankers et al. |
| 2009/0063187 | A1 | 3/2009 | Johnson et al. |
| 2009/0063402 | A1 | 3/2009 | Hayter |
| 2009/0069745 | A1 | 3/2009 | Estes et al. |
| 2009/0150865 | A1 | 6/2009 | Young et al. |
| 2009/0153058 | A1 | 6/2009 | Feng et al. |
| 2009/0156990 | A1 | 6/2009 | Wenger et al. |
| 2009/0156991 | A1 | 6/2009 | Roberts |
| 2009/0157040 | A1 | 6/2009 | Jacobson et al. |
| 2009/0157432 | A1 | 6/2009 | Palmroos et al. |
| 2009/0157695 | A1 | 6/2009 | Roberts |
| 2009/0174550 | A1 | 7/2009 | Aninye et al. |
| 2009/0177769 | A1 | 7/2009 | Roberts |
| 2009/0183105 | A1 | 7/2009 | Teel, IV et al. |
| 2009/0271729 | A1 | 10/2009 | Killoren Clark et al. |
| 2009/0275886 | A1 | 11/2009 | Blomquist et al. |
| 2009/0295569 | A1 | 12/2009 | Corwin et al. |
| 2010/0008795 | A1 | 1/2010 | DiPerna |
| 2010/0100037 | A1 | 4/2010 | Cozmi et al. |
| 2010/0121170 | A1 | 5/2010 | Rule |
| 2010/0121654 | A1 | 5/2010 | Portnoy et al. |
| 2010/0160860 | A1 | 6/2010 | Celentano et al. |
| 2010/0163613 | A1 | 7/2010 | Bucher et al. |
| 2010/0169120 | A1 | 7/2010 | Herbst et al. |
| 2010/0174229 | A1 | 7/2010 | Hsu et al. |
| 2010/0218586 | A1 | 9/2010 | Rosinko et al. |
| 2010/0271218 | A1 | 10/2010 | Hoag et al. |
| 2010/0287006 | A1 | 11/2010 | Cannon et al. |
| 2010/0292645 | A1 | 11/2010 | Hungerford et al. |
| 2010/0313105 | A1 | 12/2010 | Nekoomaram et al. |
| 2011/0006876 | A1 | 1/2011 | Moberg et al. |
| 2011/0009813 | A1 | 1/2011 | Rankers |
| 2011/0009814 | A1 | 1/2011 | Tsoukalis |
| 2011/0022981 | A1 | 1/2011 | Mahajan et al. |
| 2011/0047499 | A1 | 2/2011 | Mandro et al. |
| 2011/0072379 | A1 | 3/2011 | Gannon et al. |
| 2011/0077965 | A1 | 3/2011 | Nolte et al. |
| 2011/0078145 | A1 | 3/2011 | Chung et al. |
| 2011/0078608 | A1 | 3/2011 | Gannon et al. |
| 2011/0144574 | A1 | 6/2011 | Kamen et al. |
| 2011/0178462 | A1 | 7/2011 | Moberg et al. |
| 2011/0238032 | A1 | 9/2011 | McTaggart et al. |
| 2011/0241878 | A1 | 10/2011 | Hoag et al. |
| 2011/0259954 | A1 | 10/2011 | Bartz et al. |
| 2011/0264044 | A1 | 10/2011 | Bartz et al. |
| 2011/0290250 | A1 | 12/2011 | Olson et al. |
| 2012/0166530 | A1 | 6/2012 | Tseng |
| 2012/0179130 | A1 | 7/2012 | Barnes et al. |
| 2012/0215169 | A1 | 8/2012 | Moberg et al. |
| 2012/0220928 | A1 | 8/2012 | Estes et al. |
| 2013/0053816 | A1 | 2/2013 | DiPerna et al. |
| 2013/0064044 | A1 | 3/2013 | Carter et al. |
| 2013/0104120 | A1 | 4/2013 | Arrizza et al. |
| 2013/0138452 | A1 | 5/2013 | Cork et al. |
| 2013/0185098 | A1 | 7/2013 | Mitchel et al. |
| 2013/0190674 | A1 | 7/2013 | Case et al. |
| 2013/0197693 | A1 | 8/2013 | Kamen et al. |
| 2013/0218080 | A1 | 8/2013 | Peterfreund et al. |
| 2013/0248426 | A1 | 9/2013 | Pouchoulin |
| 2013/0253946 | A1 | 9/2013 | Broselow |
| 2013/0274644 | A1 | 10/2013 | Hertz |
| 2013/0283529 | A1 | 10/2013 | Hayes et al. |
| 2013/0317753 | A1 | 11/2013 | Kamen et al. |
| 2013/0324928 | A1 | 12/2013 | Kruse |
| 2013/0331790 | A1 | 12/2013 | Brown et al. |
| 2014/0032694 | A1 | 1/2014 | Cohn et al. |
| 2014/0039455 | A1 | 2/2014 | Miller et al. |
| 2014/0085076 | A1 | 3/2014 | Carnes |
| 2014/0188516 | A1 | 7/2014 | Kamen et al. |
| 2014/0276571 | A1 | 9/2014 | Ludolph |
| 2014/0323959 | A1 | 10/2014 | Lebel et al. |
| 2015/0154364 | A1 | 6/2015 | Biasi et al. |
| 2015/0356253 | A1 | 12/2015 | Sims et al. |
| 2015/0356255 | A1 | 12/2015 | Simpson et al. |
| 2016/0038163 | A1 | 2/2016 | Thor et al. |
| 2017/0061083 | A1 | 3/2017 | Jackson |
| 2017/0128668 | A1 | 5/2017 | Miller et al. |
| 2018/0193561 | A1 | 7/2018 | Susi |
| 2020/0023127 | A1 | 1/2020 | Simpson et al. |
| 2020/0051190 | A1 | 2/2020 | Kamen et al. |
| 2020/0206413 | A1 | 7/2020 | Silkaitis et al. |
| 2020/0357500 | A1 | 11/2020 | Rubalcaba, Jr. et al. |
| 2021/0068683 | A1 | 3/2021 | Reich |
| 2021/0146117 | A1 | 5/2021 | Reich et al. |
| 2022/0001106 | A1 | 1/2022 | DiPerna et al. |
| 2025/0032715 | A1 | 1/2025 | Dobbles et al. |

FOREIGN PATENT DOCUMENTS

| | | | | |
|---|---|---|---|---|
| CN | 101785885 | A | 7/2010 | |
| CN | 102813977 | A | 12/2012 | |
| EP | 1944709 | A1 | 7/2008 | |
| EP | 2410448 | A2 | 1/2012 | |
| JP | 2001-282922 | A | 10/2001 | |
| JP | 2007-512041 | A | 5/2007 | |
| JP | 2013-179973 | A | 9/2013 | |
| NZ | 542646 | A | 10/2008 | |
| WO | WO-00/16211 | A1 | 3/2000 | |
| WO | WO-2005/050526 | A2 | 6/2005 | |
| WO | WO-2005/056087 | A1 | 6/2005 | |
| WO | WO-2006/086735 | A2 | 8/2006 | |
| WO | WO-2006/098960 | A1 | 9/2006 | |
| WO | WO-2006/125692 | A1 | 11/2006 | |
| WO | WO-2008/059495 | A2 | 5/2008 | |
| WO | WO-2008/127694 | A1 | 10/2008 | |
| WO | WO-2010053704 | A1 * | 5/2010 | ............. G16H 70/40 |

OTHER PUBLICATIONS

Anychart. (2013). Using CSV Data. [User's Guide]. Retrieved on Dec. 7, 2025. 1 page. https://web.archive.org/web/20130120230839/

(56) References Cited

OTHER PUBLICATIONS http://www.anychart.com/products/anychart/docs/users-guide/index.html?Using-CSV-Data.html.
Baxter. (Jun. 26, 2012). "Press Release—Baxter's SIGMA Spectrum Infusion System Receives Best in KLAS Award for Second Consecutive Year." 2 pages. https://investor.baxter.com/investors/events-and-news/news/press-release-details/2012/Baxters-SIGMA-Spectrum-Infusion-System-Receives-Best-in-KLAS-Award-for-Second-Consecutive-Year/default.aspx.
Cardinal Health, (n.d.) IVAC PCAM Syringe Pump—Technical Service Manual, 1000SM00017, Issue 2 (2005-2006). 106 pages.
Cardinal Health, (n.d.). IVAC Volumetric Pump—Models 597 & 598, Technical Service Manual, 1000SM0016, Issue 3 (1998-2006). 76 pages.
CareFusion Corporation and Cerner Corporation Integrate Smart Pump Technologies to Help Improve Medication Safety and Efficiency. BioSpace. Webpage. (Apr. 19, 2012). 10 pages.
Cornell, P. (2006). "Accessing and Analyzing Data with Microsoft Excel—Charting Data." Flylib.com. 3 pages. Retrieved on Dec. 1, 2025 from https://web.archive.org/web/20121201222809/http://flylib.com/books/en/2.157.1.23/1/.
Declaration of Dr. James C. Fackler, MD FCCM Under 37 C.F.R. § 1.132 related to the Ex Parte Reexamination of U.S. Pat. No. 12,205,703, Control No. 90/015,391. Declaration dated Jan. 23, 2026. 92 pages.
Defendants Baxter Int'l and Baxter Healthcare's Reply Brief in Support of Their Motion to Dismiss for Failure to State a Claim, *Becton, Dickinson and Co. et al.* v. *Baxter Int'l Inc. et al.,* No. 1-25-cv-00591-CFC (D. Del. Aug. 29, 2025), ECF No. 31. 18 pages.
Defendants Baxter Int'l and Baxter Healthcare's Opening Brief in Support of Their Motion to Dismiss for Failure to State a Claim, *Becton, Dickinson and Co. et al.* v. *Baxter Int'l Inc. et al.,* No. 1-25-cv-00591-CVC (D. Del. Jul. 10, 2025), ECF No. 18. 29 pages.
Eckel, S.F. (2009). "Making the Case for Wireless Smart Pumps." Pharmacy Purchasing and Products Magazine, 6(12), 2-5. 3 pages. https://www.pppmag.com/article/644.
Ex Parte Reexamination Interview Summary related to U.S. Pat. No. 12,205,703, Control No. 90/015,391, mail date Jan. 15, 2026. 4 pages.
Graseby Medical Ltd. (2002). Model 3000/500 and Micro 3100/505 Volumetric Infusion Pump. Graseby Medical Ltd./Smith Medical. 231 pages.
Hollmer, M. (Mar. 9, 2012). "Hospira Receives FDA Clearance for SymbiqTM 3.13 Infusion Pump." Fierce Biotech. Questex LLC. 2 pages.
Hospira. (2006). "Symbiq System Operating Manual." Hospira, Inc. 50 pages.
Hospira. (2007). Lifecare PCA System Operating Manual. Hospira, Inc. 184 pages.
Hospira. (2008). "Symbiq System Operating Manual." Hospira, Inc. 236 pages. (Cover p. 54. 58 pages). Part 1 of 4.
Hospira. (2008). "Symbiq System Operating Manual." Hospira, Inc. 236 pages. (pp. 55-110. 56 pages). Part 2 of 4.
Hospira. (2008). "Symbiq System Operating Manual." Hospira, Inc. 236 pages. (pp. 111-165. 55 pages). Part 3 of 4.
Hospira. (2008). "Symbiq System Operating Manual." Hospira, Inc. 236 pages. (pp. 166-232. 67 pages). Part 4 of 4.
Hospira. (2009). "Symbiq Infusion System Technical Service Manual." Hospira, Inc. 127 pages. (Cover p. 7-9. 77 pages). Part 1 of 2.
Hospira. (2009). "Symbiq Infusion System Technical Service Manual." Hospira, Inc. 127 pages. (pp. 7-10-end. 50 pages). Part 2 of 2.
Hospira. (2011). "World's Leading Provider of Injectable Drugs and Infusion Technologies." Hospira 2011 Investor Day Presentation. 136 pages. https://www.sec.gov/Archives/edgar/data/1274057/000110465911050452/a11-25522_1ex99d1.htm.
Hospira. (2013). Hospira MedNet™ Safety Software Webpage, at least by Jan. 16, 2013, Hospira, Inc. 1 page. https://web.archive.org/web/20130116032341/http://hospira.com/products_and_services/clinical_software/mednet/index.
Hospira. (2013). LifeCare™ PCA Infusion System, at least by Jan. 13, 2014. Hospira, Inc. 1 page. https://web.archive.org/web/20130113072623/http://www.hospira.com/products_and_services/infusion_pumps/Lifecare/index. 1 page.
Hospira. IV clinical integration connects your care team, at least by Jun. 2012. Hospira, Inc. 1 page. https://web.archive.org/web/20120604023421/http://www.ivclinicalintegration.com/achieving-iv-clinical-integration.
Hospira. IV clinical integration leads to more efficient workflow, at least by Jun. 2012. Hospira, Inc. 1 page. https://web.archive.org/web/20120604070452/http://www.ivclinicalintegration.com/visualizing-iv-clinical-integration/workflow-comarison.
Hospira. IV clinical integration streamlines IV infusion pump programming, at least by Jun. 2012. Hospira, Inc. 1 page. https://web.archive.org/web/20120604023441/http://www.ivclinicalintegration.com/visualizing-iv-clinical-integration/auto-programming.
Hospira. IV clinical integration streamlines medication management documentation, at least by Jun. 2012 Hospira, Inc. 1 page. https://web.archive.org/web/20120616092918/http://www.ivclinicalintegration.com/visualizing-iv-clinical-integration/auto-documentation.
Hospira. Symbiq Infusion System Brochure, at least by Jan. 31, 2013. 6 pages. https://web.archive.org/web/20130131174356/http://hospira.com/Images/P11-3208_Symbiq_brochure_FINAL_32-90345_1.PDF.
Hospira. Symbiq Infusion System Webpage, at least by Jan. 16, 2013. 1 page. https://web.archive.org/web/20130116042038/http://hospira.com/products_and_services/infusion_pumps/symbiq/index.
Infusion Pumps by FDA https://www.fda.gov/medical-devices/general-hospital-devices-and-supplies/infusion-pumps (Year: 2018). 2 pages.
Institute for Safe Medication Practices (ISMP). (2009). "Proceedings from the ISMP Summit on the use of Smart Infusion Pumps: Guidelines for Safe Implementation and Use." https://www.ismp.org/sites/default/files/attachments/2018-06/ISMP%20Smart%20Pump%20Guidelines%202009.pdf. 19 pages.
Manual for "IntelliVue Patient Monitor". Philips. pp. 1-534. accessed via web: https://medaval.ie/docs/manuals/Intellivue-Manual.pdf Jan. 15, 2008. (Year: 2008).
Marino, A. (2012). White Paper. Implementing the Symbiq Infusion System with Hospira MedNet Safety Software, at least by 2012. Hospira, Inc. 5 pages.
Maxim Integrated. (May 10, 2010). "Tutorial 4677. Important Considerations for Infusion Pump and Portable Medical Designs." www.maximintegrated.com. 7 pages.
Non-Final Office Action in Ex Parte Reexamination of U.S. Pat. No. 12,205,703 dated Nov. 25, 2025. Control No. 90/015391. 62 pages.
Order Granting Request for Ex Parte Reexamination of U.S. Pat. No. 12,205,703 issued Jan. 21, 2025. Control No. 90/015,391. Order issued Aug. 14, 2025, 25 pages.
Pettus, D.C, & Vanderveen, T. (Nov./Dec. 2013). "Worth the Effort? Closed-Loop Infusion Pump Integration with the EMR." Biomedical Instrumentation & Technology. 467-477. 11 pages.
Phelps, P.K. (2011). "Smart Infusion Pumps: Implementation, Management, and Drug Libraries." American Society of Health-System Pharmacists. Bethesda, MD. 91 pages.
Plaintiffs' Answering Brief in Opposition to Defendants' Motion to Dismiss Pursuant to Fed R. Civ. P. 12(b)(6), *Becton, Dickinson and Co. et al.* v. *Baxter Int'l, Inc. et al.,* No. 1-25-cv-00591-CFC (D. Del. Aug. 11, 2025), ECF No. 26. 34 pages.
Questex. (Dec. 14, 2010). "Smiths Medical Introduces Wireless Version of the Medfusion Syringe Infusion System" Health Tech, Questex LLC. 2 pages.
Request for Ex Parte Reexamination of U.S. Pat. No. 12,205,703 issued Jan. 21, 2025. Request filed Jul. 16, 2025, assigned Control No. 90/015,391. 72 pages.
Response to Office Action in Ex Parte Reexamination of U.S. Pat. No. 12,205,703 dated Nov. 25, 2025. Control No. 90/015391. Response date Jan. 23, 2026. 28 pages.
Ruth, C., Vogler, A. & Karsten, W. (Aug. 18, 2006). "Ambient Light Sensors SFH3410, SFH3710." Osram Opto Semiconductors [Application Note] 9 pages.

(56) References Cited

OTHER PUBLICATIONS

Sigma International, Inc. (Aug. 2008). Sigma Spectrum Infusion Pump Service Manual. P/N 41019. (Rev. T). 56 pages.
Sigma International, Inc. (Aug. 2009). Sigma Spectrum Infusion Pump Service Manual. P/N 41019. (Rev. W). 58 pages.
Sigma International. (May 15, 2008). sigmaspectrum operator's manual. Sigma P/N 41018. (Rev. X). 63 pages.
Sigma International. (Oct. 8, 2009). sigmaspectrum operator's manual. Sigma P/N 41018. (Rev. AL). 72 pages.
Sigma International. Sigma Spectrum Specifications, at least by Dec. 5, 2012. Sigma, International. Retrieved on Dec. 2, 2025 from https://web.archive.org/web/20121205151657/http:/www.sigmapumps.com/products/spectrum/specifications/. 2 pages.
Sigma, LLC. (2010). sigmaspectrum Operator's Manual 35700ABB & 35700BAX. Sigma Manual No. 41018. (Rev. AR). 102 pages.
Sigma, LLC. (2010). sigmaspectrum Service Manual 35700ABB & 35700BAX. Sigma Manual No. 41019. (Rev. AA). 68 pages.
Sigma, LLC. (2011). sigmaspectrum Operator's Manual 35700BAX & 35700ABB. Manual 41018-6.05/6.2.4. (Rev. C). 119 pages.
Sigma, LLC. (2011). sigmaspectrum Operator's Manual 35700BAX & 35700ABB. Manual 41018-6.05/6.2.4. (Rev. D). 125 pages.
Sims, N. et al. (2011). "Chapter 17—Drug Infusion Pumps in Anesthesia, Critical Care, and Pain Management." In Sandberg, W., Urman R.D., and Ehrenfeld, J.M. (Eds.), The MGH Textbook of Anesthetic Equipment. pp. 236-246. Churchill Livingston. https://doi.org/10.1016/B978-1-4377-0973-5.10017-9. 11 pages.
Smiths Medical ASD, Inc. (Aug. 29, 2011). Medfusion 4000 Syringe Infusion Pump and Medication Safety Software FDA 510(k) Summary (510(k): K111386). [date prepared Aug. 24, 2011]. 10 pages.
Smiths Medical. (2006). "The Medfusion PharmGuard Medication Safety System." Software Product Brochure. 8 pages. Smiths Medical ASD, Inc. (https://web.archive.org/web/20111120133119/http://smiths-medical.com/upload/products/pdf/193800-IS400%20Medfusion3500%20Family.pdf).
Smiths Medical. (Sep. 26, 2011). "FDA Clearance for Smiths Medicals Wireless Medfusion 4000 Syringe System." Smiths Group. 5 pages.
Smiths Medical. (2011). "Medfusion 4000 Syringe Infusion Pump with PharmGuard Infusion Management Software Suite." Product Brochure. Smiths Medical ASD, Inc. 2 pages. (https://web.archive.org/web/20120715033132/http://www.smiths-medical.com/upload/products/pdf/IN193825%20-%20Medfusion%204000%20&%20PharmGuard%20Software%20Suite%20Sell%20Sheet.pdf).
Smiths Medical. (2011). Medfusion 4000 Syringe Infusion Pump Operator's Manual. Smiths Medical ASD, Inc. 154 pages. (Cover p. 23. 27 pages). Part 1 of 5.
Smiths Medical. (2011). Medfusion 4000 Syringe Infusion Pump Operator's Manual. Smiths Medical ASD, Inc. 154 pages. (pp. 24-58. 35 pages). Part 2 of 5.
Smiths Medical. (2011). Medfusion 4000 Syringe Infusion Pump Operator's Manual. Smiths Medical ASD, Inc. 154 pages. (pp. 59-92. 34 pages). Part 3 of 5.
Smiths Medical. (2011). Medfusion 4000 Syringe Infusion Pump Operator's Manual. Smiths Medical ASD, Inc. 154 pages. (pp. 93-121. 29 pages). Part 4 of 5.
Smiths Medical. (2011). Medfusion 4000 Syringe Infusion Pump Operator's Manual. Smiths Medical ASD, Inc. 154 pages. (pp. 122-150. 29 pages). Part 5 of 5.
Smiths Medical. (2011). PharmGuard Server Infusion Management Software—Specifications. Smiths Medical ASD, Inc. 2 pages. (https://web.archive.org/web/20120715022244/http://www.smiths-medical.com/upload/products/pdf/IN193822.pdf).
Smiths Medical. (2012). "Infusion Syringe Pump Software—PharmGuard Medication Safety Software." Smiths Medical. Webpage, published by at least May 11, 2012. 8 pages. (https://web.archive.org/web/20120511173424/http://www.smiths-medical.com/catalog/syringe-pump-software/pharmguard-medication-safety-software/pharmguard-medication-safety-software.html).
Smiths Medical. (2012). "Infusion Syringe Pump Software—PharmGuard Server Infusion Management Software." Smiths Medical. Webpage, published by at least May 11, 2012. 9 pages. (https://web.archive.org/web/20120511041834/http://www.smiths-medical.com/catalog/syringe-pump-software/pharmguard-server/pharmguard-server-infusion-management.html).
Smiths Medical. (2012). Infusion Syringe Pump Systems—Medfusion 4000 Wireless Syringe Infusion Pump, published by at least Apr. 20, 2012. Smiths Medical. 8 pages. (https://web.archive.org/web/20120420044256/http://www.smiths-medical.com/catalog/syringe-pump/medfusion-4000-syringe-pump/medfusion-4000-wireless-syringe.html).
Soneira, R.M. (2010). "Apple iphone 3GS LCD Display Shoot-Out." DisplayMate Technologies Corporation. Retrieved on Dec. 6, 2025 from https://www.displaymate.com/iPhone_3GS_ShootOut.htm. 8 pages.
Toshiba Corporation. (2009). Integrated High Definition LCD Television. [Owner's Manual]. Toshiba America Consumer Products, L.L.C. 70 pages.
Vanderveen, T. (Feb. 27, 2012). "A Decade of 'Smart' Infusion Pumps." Pharmacy Times, 78(2), Retrieved Nov. 30, 2025 from https://www.pharmacytimes.com/view/a-decade-of-smart-infusion-pumps. 2 pages.
Vanderveen, T. (May/Jun. 2006). "IVs First: A New Barcode Implementation Strategy." Patient Safety & Quality Healthcare. Retrieved Nov. 30, 2025. From https://www.psqh.com/mayluno6/ivs.html. 5 pages.
Wilson, N. (Feb. 4, 2019). "Enhancing DERS through smart pump-EMR Integration." Becton, Dickinson and Company. Retrieved Nov. 30, 2025 from https://www.bd.com/en-us/resource-and-education/documentation-landing-page/blogs/enhancing-ders-through-smart-pump-emr-integration0. 5 pages.
Final Office Action issued in the Ex Parte Reexamination of U.S. Pat. No. 12,205,703, mail date Mar. 11, 2026. Control No. 90/015,391. 81 pages.
Defendants Baxter Int'l and Baxter Healthcare's Invalidity Contentions, *Becton, Dickinson and Co et al.*v. *Baxter Int'l Inc. et al.*, No. 1-25-cv-00591-CFC. Dec 9, 2025. 193 pages. Redacted.
Ex Parte Reexamination Interview Summary related to U.S. Pat. No. 12,205,703, Control No. U.S. Appl. No. 90/015,391, mail date May 6, 2026. 7 pages.
EXHIBIT 703-1: Invalidity Contentions Claim Chart for U.S. Pat. No. 12,205,703 in light of Evans (U.S. Pat. Pub. No. US 2008/0033360). Dec. 9, 2025. 358 pages.
EXHIBIT 703-2: Invalidity Contentions Claim Chart for U.S. Pat. No. 12,205,703 in light of Alberti (U.S. Pat. Pub. No. US 2008/0200868). Dec. 9, 2025. 404 pages.
EXHIBIT 703-3: Invalidity Contentions Claim Chart for U.S. Pat. No. 12,205,703 in light of Symbiq. Dec. 9, 2025. 347 pages.
Response to Ex Parte Reexamination Interview Summary related to U.S. Pat. No. 12,205,703 and Notice of Appeal From The Examiner To The Patent Trial And Appeal Board. Control No. U.S. Appl. No. 90/015,391. Response and Appeal file date May 11, 2026. 10 pages.
Request for Ex Parte Reexamination of U.S. Pat. No. 12,205,700 issued Jan. 21, 2025. Request filed Jun. 9, 2026, assigned Control No. U.S. Appl. No. 90/016,389. 54 pages.

* cited by examiner

DISPLAYING VISUAL ELEMENTS ON A MEDICAL DEVICE

CROSS REFERENCE TO RELATED APPLICATIONS

This application is a continuation of U.S. patent application Ser. No. 18/978,664 filed on Dec. 12, 2024, which is a continuation of U.S. patent application Ser. No. 18/678,556 filed May 30, 2024, entitled DISPLAYING VISUAL ELEMENTS ON A MEDICAL DEVICE, now U.S. Pat. No. 12,205,703, which is a continuation of U.S. patent application Ser. No. 17/539,526, filed Dec. 1, 2021, entitled DISPLAYING VISUAL ELEMENTS ON A MEDICAL DEVICE, now U.S. Pat. No. 12,205,700, which is a continuation of U.S. patent application Ser. No. 15/930,270 filed May 12, 2020, entitled DISPLAYING VISUAL ELEMENTS ON A MEDICAL DEVICE, now U.S. Pat. No. 11,217,338, which is a continuation of U.S. patent application Ser. No. 16/197,121 filed Nov. 20, 2018, entitled DISPLAYING VISUAL ELEMENTS ON A MEDICAL DEVICE, now U.S. Pat. No. 10,664,147, which is a continuation of U.S. patent application Ser. No. 14/939,875, filed Nov. 12, 2015, entitled DISPLAYING VISUAL ELEMENTS ON A MEDICAL DEVICE, now U.S. Pat. No. 10,140,004, which is a continuation of U.S. patent application Ser. No. 12/987,472, filed Jan. 10, 2011, entitled DISPLAYING VISUAL ELEMENTS ON A MEDICAL DEVICE, now U.S. Pat. No. 9,190,010, the disclosures of which are incorporated herein by reference in their entireties.

BACKGROUND

A display screen on a medical device allows for a clinician to visibly see some parameters of the medical device. However, adjustments of the display screen typically does not allow for optimal viewability. In particular, current medical devices do not allow for color customization to inform the user of how the medical device operates.

The drawings referred to in this description should be understood as not being drawn to scale except if specifically noted.

DESCRIPTION OF EMBODIMENTS

Reference will now be made in detail to embodiments of the present technology, examples of which are illustrated in the accompanying drawings. While the technology will be described in conjunction with various embodiment(s), it will be understood that they are not intended to limit the present technology to these embodiments. On the contrary, the present technology is intended to cover alternatives, modifications and equivalents, which may be included within the spirit and scope of the various embodiments as defined by the appended claims.

Furthermore, in the following description of embodiments, numerous specific details are set forth in order to provide a thorough understanding of the present technology. However, the present technology may be practiced without these specific details. In other instances, well known methods, procedures, components, and circuits have not been described in detail as not to unnecessarily obscure aspects of the present embodiments.

The description below will first describe the components of medical system 100. The description will then describe the functionality of the components during use of medical system 100.

In general, medical system 100 allows for detailed configuration of the appearance of a display to ensure optimal viewability and display perception based on clinical practices and preferences. Moreover, adjustments are made based on environment. As a result, errors are reduced and care is improved.

In contrast, conventional systems have minimal configurability. For example, backlight and contrast level may be adjusted. However, the adjustments do not give optimal viewability for the light conditions. Moreover, the conventional systems don't allow for customization, such as color, to inform the user of how the device is configured to operate.

Figure 1:
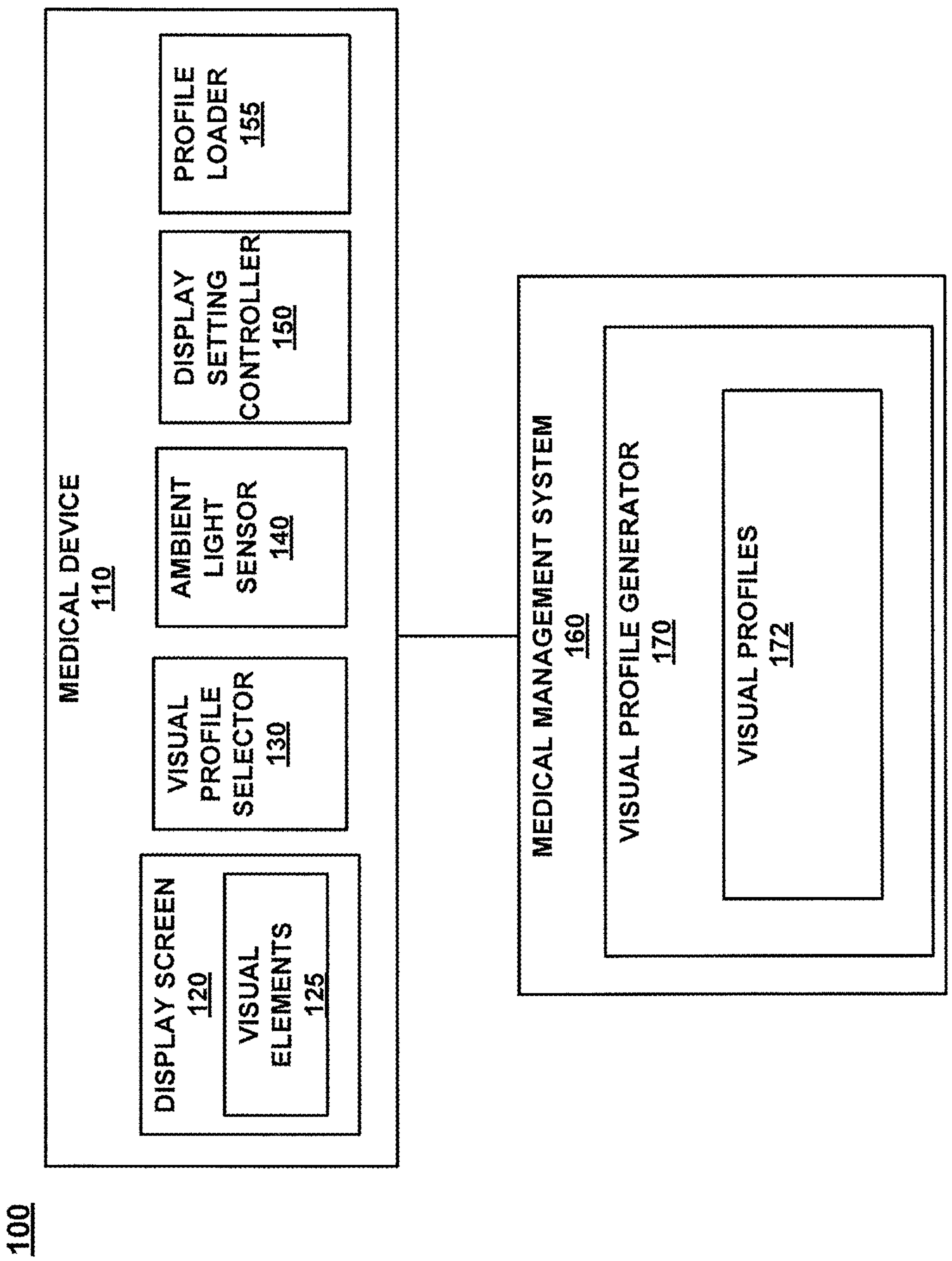
FIG. 1 illustrates an example of a medical system, in accordance with an embodiment of the present invention.

FIG. 1 depicts an embodiment of medical system 100. Medical system 100 includes medical device 110 and medical management system 160. In one embodiment, medical system 100 is a medication delivery system. In such an embodiment, medical device 110 is an infusion pump.

Medical management system 160 includes visual profile generator 170 and visual profiles 172. Visual profile generator 170 is for generating visual profiles 172. Visual profiles 172 are configured for facilitating in the control of the visual appearance of visual elements 125, which will be described in detail below.

Medical device 110 includes display screen 120, visual profile selector 130, ambient light sensor 140, display setting controller 150, and profile loader 155.

Display screen 120 is for displaying visual elements 125. Display screen 120 can be any display screen able to display visual elements 125. For example, display screen 120 is a color display screen for displaying visual elements 125.

Visual elements 125 are associated with functions of medical device 110. For example, visual elements 125 are associated with functions such, as but not limited to, parameters, medicine, or medicine dosage. Visual elements 125 can include icons, images, textures, fonts, etc., based on workflow, user inputs (e.g., user input fields), graphical libraries, etc.

Figure 2:
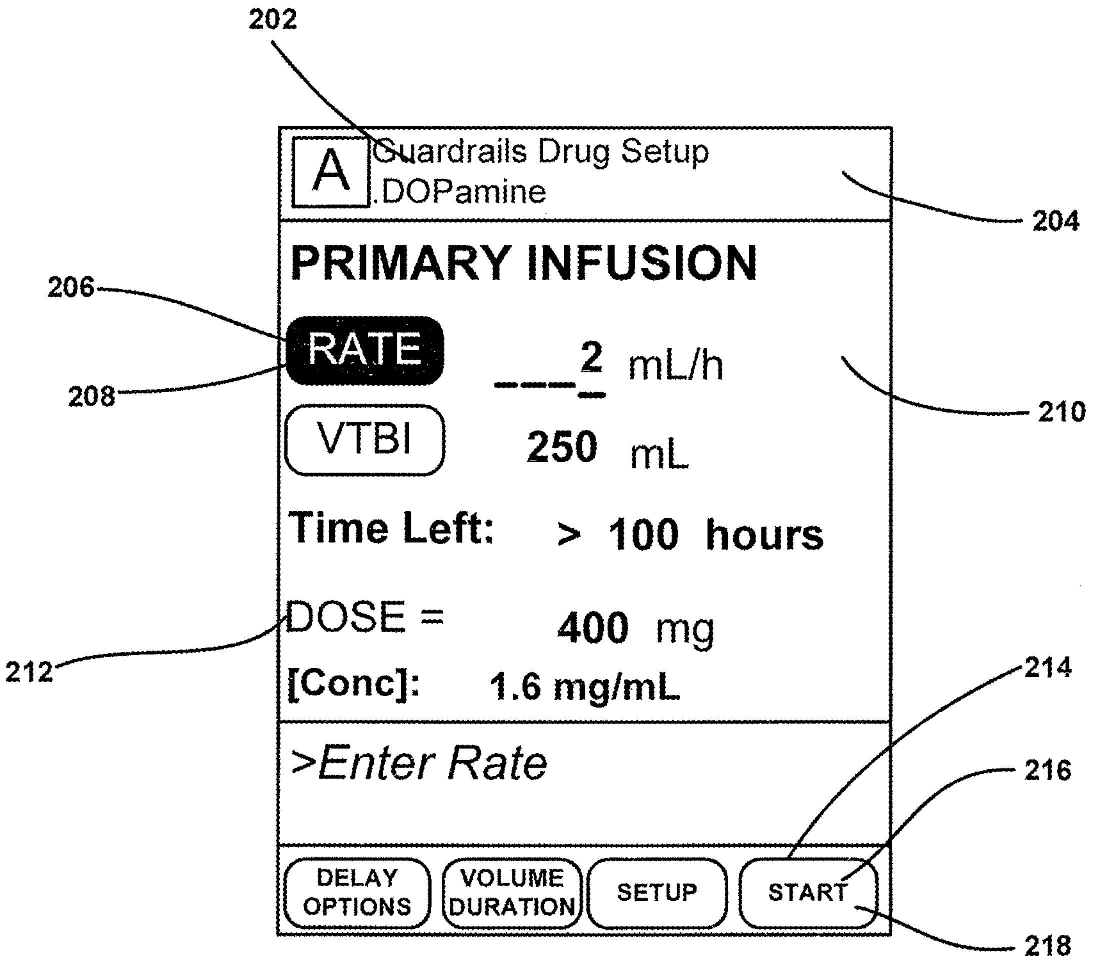
FIG. 2 illustrates an example of visual elements, in accordance with an embodiment of the present invention.

FIG. 2 depicts an embodiment of visual elements 125 displayed on display screen 120. In this embodiment, visual elements 125 include title bar text color 202, title bar color 204, selected button text color 206, selected button color 208, background color 210, text color 212, button border color 214, button text color 216 and button color 218. It should be appreciated that the number of elements and their definitions can vary depending on the graphical user interface engine (not shown) that is used to render visual elements 125 on display screen 120.

Visual profiles 172 facilitate in the control of the visual appearance of visual elements 125, as described above. In other words, visual profiles manage the visual configurations of visual elements 125 to enhance safe use of system 100. Also, the visual configuration of visual elements 125 enable power saving of medical device 110.

In general, visual profiles 172 allow for the customization of the visual performance of display screen 120. For example, visual profiles 172 allow for the visual customization (e.g., color customization) of visual elements 125.

Visual profiles 172 depend on, among other things, criticality, classification, state of the device, state of the patient (e.g. heart rate), device association, state of the device class, clinical workflow, care area, clinical practices, environment (ambient light), device capabilities etc.

Visual profiles 172 include, but are not limited to, a color, a pattern, a bitmap, a texture or a theme.

In various embodiments, visual profiles 172 utilize a color space. For example, a RGB color space, CMYC color space or an HSV color space. Colors associated with visual profiles 172 can be a combination of a base color from a color space modified by adding contrast, brightness or saturation, by configuration or in conjunction with sensed ambient light.

In one embodiment, visual profiles 172 include a color profile, which is a set of color configuration vectors that comprise each color region. The color regions are represented by a color configuration vector that specifies the perceived color of the region. The color profile, P is defined by the set:

$$P = \{C_{R1}, C_{R2} \ldots C_{Rn}\}. \tag{1}$$

The configuration parameters for a particular color region to be display on display screen 120 is represented by a configuration vector, $$C_R = \{I_R, I_G, I_B, B_L\}, \tag{2}$$

where $I_R$, $I_G$, $I_B$ are the intensity of the red, green and blue color channels making the color, and $B_L$ is the intensity of the backlight. Although $B_L$ can be configured individually per color (in equation 2), limitations on backlight devices often require the $B_L$ parameter to be the same for all regions on the display screen at a given point in time, which is the case in this embodiment.

Accordingly, the color profile is, $$P = \{B_L, C'_{R1}, C'_{R2} \ldots C'_{Rn}\}, \tag{3}$$

where $C'_R$ is the color vector CR without the individual configuration parameter $B_L$ present.

Visual profile selector 130 is for selecting visual profiles 172 based on a state of medical system 100 and/or medical device 110. States of medical system 100 and/or device 110 can be, but are not limited to, care area, power state, clinician, clinician preferences, patient, ambient light, alarm settings, infusing, priming, maintenance mode, pressure limits and pump orientation. In various embodiments, the states are dynamic.

For example, a first medical device is assigned to a male patient, and a second medical device is assigned to a female patient As such, visual profile selector 130 of the first medical device selects visual profiles 172 (e.g., a blue color) based on the first medical device assigned to the male patient. Likewise, visual profile selector 130 of the second medical device selects visual profiles 172 (e.g., a pink color) based on the second medical device assigned to the female patient.

In one embodiment, visual profile selector 130 utilizes a rule engine to select a visual profile. In such an embodiment, a rule may be stored in plain text or structured text, such as XML, which can be updated dynamically. For example, a rule can be, that if the current care area is "Neonatal," then use Profile 1, or if the current care area is "ICU, then use profile 2.

As a result, visual elements 125 of the first medical device for the male patient are customized with a blue color. Similarly, visual elements 125 of the second medical device are customized with a pink color.

Moreover, visual profiles 172 based on the second medical device assigned to the female patient could also include a texture, such as parallel stripes. Accordingly, visual elements 125 of the second medical device are customized with a pink color with parallel stripes.

Additionally, visual profile selector 130 selects a visual profile of the visual profiles 172 based on the system state and applies the visual profile to an active profile. In one embodiment, visual profiles 172 are processed at run time to adjust to changes in ambient light.

In one embodiment, the aggregate state of medical device 110 is the sum of the state of medical device 110 and clinical configurations. It should be appreciated that an active profile can contain visual configurations from multiple visual profiles. In various embodiments, a visual profile includes visual configurations from multiple visual profiles. Also, sub-system states are prioritized to achieve the safest active profile based on inputs to medical device 110.

In various embodiments, visual profiles 172 includes rules. For example, if a patient's pulse rate is greater than X and care area is C, then visual profile 1 is selected. However, if the care area B, then visual profile 2 is selected. Accordingly, profile selector 130 utilizes rules based on the states, mentioned above, to select the appropriate visual profile.

Visual profiles 172 can be set by a pharmacy, hospital practices, biomed, clinician, and the like. In one embodiment, the pharmacy and hospital practices are a part of a drug library.

In one embodiment, visual profiles 172 are stored on memory (not shown) in medical management system 160. In another embodiment, visual profiles 172 are stored in memory (not shown) on medical device 110. For example, visual profiles 172 are a part of a firmware image or transferred from medical management system 160 through a data port and stored into memory of medical device 110. In another embodiment, visual profiles 172 may be accessed from a portable device (e.g., PDA, tablet, etc).

In various embodiments, visual profiles 172 are activated by applying the parameters in the profiles to different subsystems using a memory bus. The parameters are sent from memory to a graphical user interface engine which executes within a microprocessor. The interface engine applies the visual information (e.g., colors) to different visual elements 125 that are viewed on display 120 and then sends the updated screens to display 120.

Profile loader 150 is for managing a set of currently available visual profiles 172. For example, profile loader 150 coordinates uploading of new profiles from medical management system 160. Moreover, profile loader 150 allows modifications to visual profiles 172 made by a user locally on medical device 110.

Display setting controller 150 is for controlling the settings of display screen 120. For example, display setting controller 150 controls the display settings (e.g., backlight, contrast, etc.) in response to ambient light detected by ambient light sensor 140.

Figure 3:
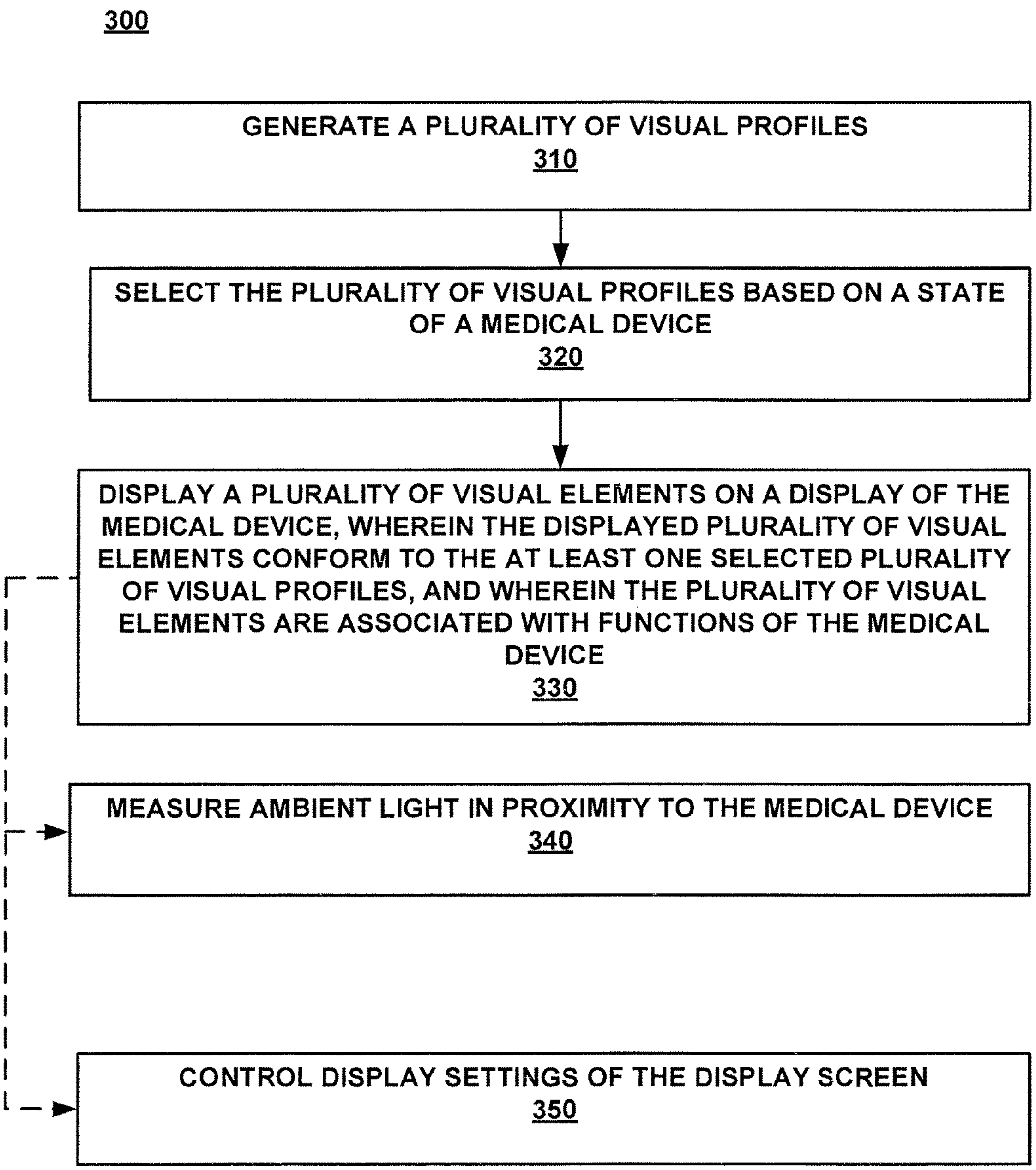
FIG. 3 illustrates a method for displaying visual elements, in accordance with an embodiment of the present invention.

FIG. 3 depicts an embodiment of a method 300 for displaying visual elements. In various embodiments, method 300 is carried out by processors and electrical components under the control of computer readable and computer executable instructions. The computer readable and computer executable instructions reside, for example, in a data storage medium such as computer usable volatile and non-volatile memory. However, the computer readable and computer executable instructions may reside in any type of computer readable storage medium. In some embodiments, method 300 is performed at least by position medical system 100, as described in FIGS. 1 and 2.

At 310 of method 300, a plurality of visual profiles are generated. For example, visual profiles 172 are generated by visual profile generator 170.

At 320, the plurality of visual profiles are selected based on a state of a medical device. For example, a visual profile including a bitmap of animal is selected based on patient associated with medical device 110. Moreover, a visual profile including a red color is selected for when medical device 110 is infusing medication to the patient.

At 330, a plurality of visual elements are displayed on a display of the medical device, wherein the displayed plurality of visual elements conform to the at least one selected plurality of visual profiles, and wherein the plurality of visual elements are associated with functions of the medical device.

Continuing the example from above, displayed background color 210 is a bitmap of an animal because the background conforms to the visual profile that includes the bitmap of the animal. Similarly, text color 212 is red because the text color of the "dose" conforms to the visual profile that includes a red color for infusing medication to the patient.

In one embodiment, at 340, ambient light is measured in proximity to the medical device. For example, ambient light is measured by ambient light sensor 140.

In another embodiment, at 350, display settings of the display screen are controlled. For example, contrast and/or backlight is adjusted by display setting controller 150 based on the ambient light measured by ambient light sensor 140.

Various embodiments of the present invention are thus described. While the present invention has been described in particular embodiments, it should be appreciated that the present invention should not be construed as limited by such embodiments, but rather construed according to the following claims.

What is claimed is:

1. An infusion pump comprising:
- a multi-color display configured to display a plurality of visual elements wherein at least two visual elements of the plurality of visual elements are associated with a function of the infusion pump;
- an ambient light sensor;
- a processor; and
- a non-transitory memory storing executable instructions that, when executed by the processor, cause the infusion pump to:
- determine a state of the infusion pump corresponding to an operating parameter associated with a treatment provided by the infusion pump;
- determine that a rule for selection of a visual profile of the infusion pump is satisfied based on the state of the infusion pump, wherein the visual profile of the infusion pump relates to a hospital care area;
- activate a visual profile of the infusion pump based on the rule for selection of the visual profile;
- display a first visual element according to the visual profile on the multi-color display of the infusion pump;
- receive a signal generated by the ambient light sensor; and
- adjust a brightness of the multi-color display based on the signal generated by the ambient light sensor.

2. The infusion pump of claim 1, wherein the rule for selection of the visual profile of the infusion pump is satisfied when the infusion pump is moved to a new hospital care area.

3. The infusion pump of claim 1, wherein the executable instructions, when executed by the processor, cause the infusion pump to present a user interface to receive an operating parameter.

4. The infusion pump of claim 1, wherein the plurality of visual elements are selected from a group consisting of: text, a text color, a title bar, title bar text, a title bar background, a button border color, a button text color, a button color, a selected button text color, a selected button color, a work flow, one or more input fields, a graphical library, one or more textures, one or more background images, and one or more grayscale patterns.

5. The infusion pump of claim 1, wherein, the visual elements correspond to a color and at least one other visual element other than a color.

6. The infusion pump of claim 1, further comprising a pressure sensor configured to generate a signal indicating a pressure condition for a fluid pathway of an infusion provided by the infusion pump and wherein the plurality of visual elements include a pressure element having a pressure element color,
- wherein the executable instructions, when executed by the processor, cause the infusion pump to:
- determine an alarm setting of the infusion pump, the alarm setting being based on the pressure condition and the operating parameter associated with the treatment provided by the infusion pump;
- automatically determine a criticality for the alarm setting;
- automatically activate a second visual profile of the infusion pump based on the criticality for the alarm setting and an additional rule for selection of the second visual profile, the second visual profile including a color selection for the pressure element color;
- display, on the color display of the infusion pump, the pressure element using the color selection.

7. The infusion pump of claim 6, wherein the executable instructions, when executed by the processor, cause the infusion pump to:
- adjust a brightness of the pressure element based on the signal generated by the ambient light sensor.

8. The infusion pump of claim 1, wherein the executable instructions, when executed by the processor, cause the infusion pump to:
- receive a user input designating the hospital care area where the infusion pump will administer the treatment.

9. The infusion pump of claim 1, wherein the executable instructions, when executed by the processor, cause the infusion pump to:
- receive a user input identifying a clinician;
- determine, based on the user input identifying clinician, that an additional rule for selection of a third visual profile is satisfied;
- activate, based on the additional rule for selection of the third visual profile, a visual profile of the infusion pump based on the clinician identification; and
- display, on the multi-color display of the infusion pump, a visual element according to the visual profile based on the clinician identification.

10. The infusion pump of claim 1, wherein the executable instructions, when executed by the processor, cause the infusion pump to:

receive a user input identifying the hospital care area;

determine that an additional rule for selection of a fourth visual profile is satisfied based on the identified hospital care area;

activate the fourth visual profile of the infusion pump based on the hospital care area and based on the additional rule for selection of the fourth visual profile; and display a visual element based on the fourth visual profile of the infusion pump on the multi-color display of the infusion pump.

11. An infusion pump comprising:

a multi-color display configured to display a plurality of visual elements wherein at least two visual elements of the plurality of visual elements are associated with a function of the infusion pump, the visual elements corresponding to a color and at least one other visual element other than a color and wherein the plurality of visual elements include a pressure element having a pressure element color;

an ambient light sensor;

a processor, a pressure sensor configured to generate a signal indicating a pressure condition for a fluid pathway of a treatment provided by the infusion pump; and a non-transitory memory storing executable instructions that, when executed by the processor, cause the infusion pump to:

determine a state of the infusion pump corresponding to an operating parameter associated with a treatment provided by the infusion pump;

determine that a rule for selection of a visual profile of the infusion pump is satisfied based on the state of the infusion pump, wherein the visual profile of the infusion pump relates to a hospital care area;

activate a visual profile of the infusion pump based on the rule for selection of the visual profile;

display a first visual element of the plurality of visual elements according to the visual profile and a second visual element of the plurality of visual elements according to the visual profile on the multi-color display of the infusion pump, the first visual element corresponding to a color and the second visual element being other than a color;

receive a signal generated by the ambient light sensor;

adjust a brightness of the multi-color display based on the signal generated by the ambient light sensor;

determine an alarm setting of the infusion pump, the alarm setting being based on the pressure condition and the operating parameter associated with the treatment provided by the infusion pump;

automatically determine a criticality for the alarm setting;

automatically activate a second visual profile of the infusion pump based on the criticality for the alarm setting and an additional rule for selection of the second visual profile, the second visual profile including a color selection for the pressure element color;

display the pressure element using the color selection on the multi-color display of the infusion pump.

12. The infusion pump of claim 11, wherein the rule for selection of the visual profile of the infusion pump is satisfied when the infusion pump is moved to a new hospital care area.

13. The infusion pump of claim 11, wherein the executable instructions, when executed by the processor, cause the infusion pump to present a user interface to receive an operating parameter.

14. The infusion pump of claim 11, wherein the plurality of visual elements are selected from a group consisting of: text, a text color, a title bar, title bar text, a title bar background, a button border color, a button text color, a button color, a selected button text color, a selected button color, a work flow, one or more input fields, a graphical library, one or more textures, one or more background images, and one or more grayscale patterns.

15. The infusion pump of claim 11, wherein the executable instructions, when executed by the processor, cause the infusion pump to: display, on the color display of the infusion pump, an icon to indicate the cause of the alarm setting.

16. The infusion pump of claim 15, wherein the executable instructions, when executed by the processor, cause the infusion pump to:

adjust a brightness of the pressure element based on the signal generated by the ambient light sensor.

17. The infusion pump of claim 11, wherein the executable instructions, when executed by the processor, cause the infusion pump to:

receive a user input designating the hospital care area where the infusion pump will administer the treatment.

18. The infusion pump of claim 11, wherein the executable instructions, when executed by the processor, cause the infusion pump to:

receive a user input identifying a clinician;

determine, based on the user input identifying clinician, that an additional rule for selection of a third visual profile is satisfied;

activate, based on the additional rule for selection of the third visual profile, a visual profile of the infusion pump based on the clinician identification; and display, on the multi-color display of the infusion pump, a visual element according to the visual profile based on the clinician identification.

19. The infusion pump of claim 11, wherein the executable instructions, when executed by the processor, cause the infusion pump to:

receive a user input identifying the hospital care area;

determine that an additional rule for selection of a fourth visual profile is satisfied based on the identified hospital care area;

activate the fourth visual profile of the infusion pump based on the hospital care area and based on the additional rule for selection of the fourth visual profile; and display a visual element based on the fourth visual profile of the infusion pump on the multi-color display of the infusion pump.

20. The infusion pump of claim 11, wherein the executable instructions, when executed by the processor, cause the infusion pump to:

determine, based on a drug library, that a second rule for selection of the visual profile is satisfied;

activate, based on the second rule for selection of the visual profile, a visual profile of the infusion pump based on the drug library; and display, on the multi-color display, the visual profile based on the drug library.

21. An infusion pump comprising:

a color display configured to display a plurality of visual elements, wherein the plurality of visual elements include a pressure element having a color;

a pressure sensor configured to generate a signal indicating a pressure condition for a fluid pathway of a treatment provided by the infusion pump;

an ambient light sensor;

a processor; and a non-transitory memory storing executable instructions that, when executed by the processor, cause the infusion pump to:

determine an alarm setting of the infusion pump, the alarm setting being based on the pressure condition and an operating parameter associated with the treatment provided by the infusion pump;

automatically determine a criticality for the alarm setting;

automatically activate a visual profile of the infusion pump based on the criticality and a rule for selection of a visual profile, the visual profile including a color selection for the color and relating to a hospital care area;

display the pressure element using the color selection on the color display of the infusion pump;

receive a signal generated by the ambient light sensor; and adjust a brightness of the color display based on the signal generated by the ambient light sensor.

22. The infusion pump of claim 21, wherein the state of the infusion pump relates to the hospital care area.

23. The infusion pump of claim 21, wherein the executable instructions, when executed by the processor, cause the infusion pump to present a user interface to receive the operating parameter.

24. The infusion pump of claim 21, wherein the plurality of visual elements are selected from a group consisting of: text, a text color, a title bar, title bar text, a title bar background, a button border color, a button text color, a button color, a selected button text color, a selected button color, a work flow, one or more input fields, a graphical library, one or more textures, one or more background images, and one or more grayscale patterns.

25. The infusion pump of claim 21, wherein, the visual elements correspond to a color and at least one other visual element other than a color.

26. The infusion pump of claim 21, wherein the executable instructions, when executed by the processor, cause the infusion pump to:

receive a user input designating the hospital care area where the infusion pump will administer the treatment.

27. The infusion pump of claim 21, wherein the executable instructions, when executed by the processor, cause the infusion pump to:

receive a user input identifying a clinician;

determine, based on the user input identifying clinician, that an additional rule for selection of a second visual profile is satisfied;

activate, based on the additional rule for selection of the second visual profile, a visual profile of the infusion pump based on the clinician identification; and display, on the color display of the infusion pump, a visual element according to the visual profile based on the clinician identification.

28. The infusion pump of claim 21, wherein the executable instructions, when executed by the processor, cause the infusion pump to:

receive a user input identifying the hospital care area;

determine that an additional rule for selection of a third visual profile is satisfied based on the identified hospital care area;

activate the third visual profile of the infusion pump based on the hospital care area and based on the additional rule for selection of the third visual profile; and display a visual element based on the third visual profile of the infusion pump on the display of the infusion pump.

29. The infusion pump of claim 21, wherein the executable instructions, when executed by the processor, cause the infusion pump to: display, on the color display of the infusion pump, an icon to indicate the cause of the alarm setting.

30. The infusion pump of claim 21, wherein the executable instructions, when executed by the processor, cause the infusion pump to: display, on the color display of the infusion pump, an icon to indicate the criticality of the alarm setting.

* * * * *